Figure 1:
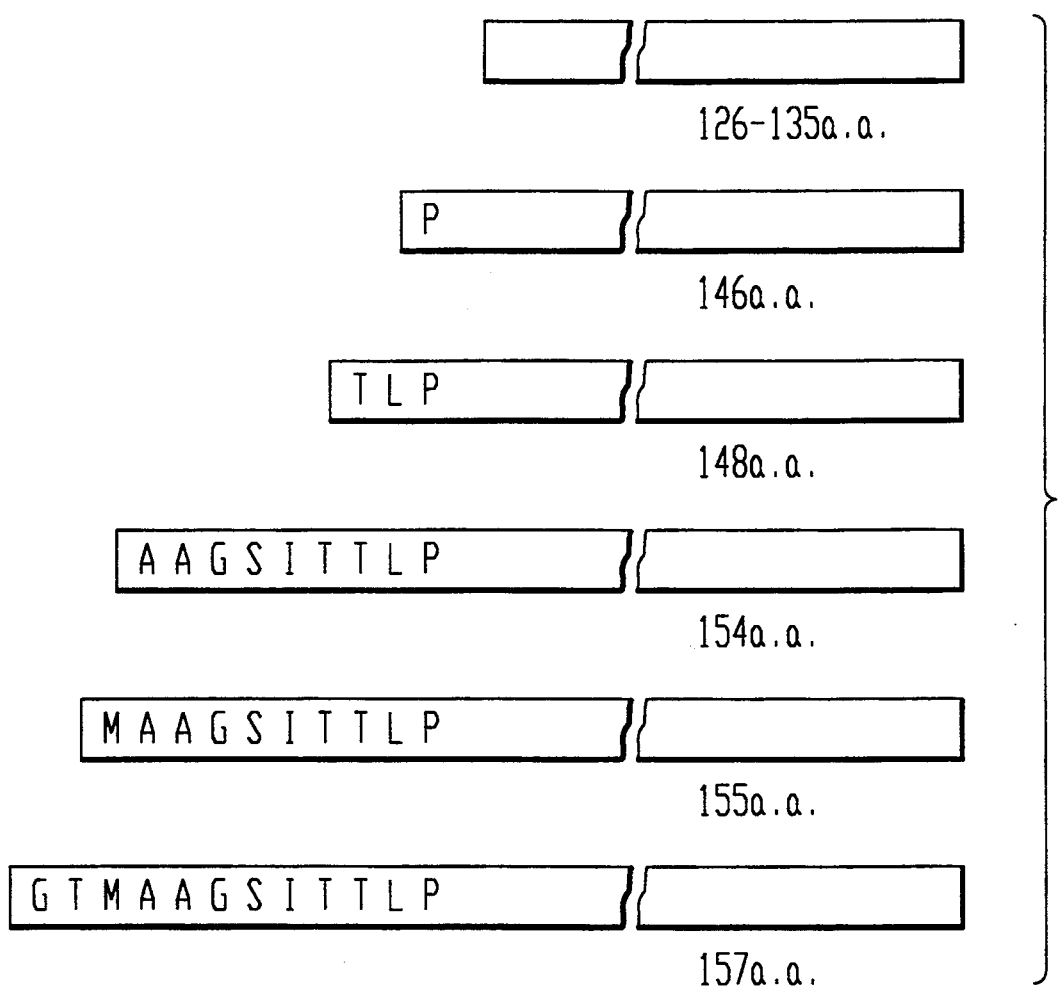

United States Patent [19]
Bergonzoni et al.

[11] Patent Number: 5,352,589
[45] Date of Patent: Oct. 4, 1994

[54] DELETION MUTANT OF BASIC FIBROBLAST GROWTH FACTOR AND PRODUCTION THEREOF

[75] Inventors: Laura Bergonzoni; Antonella Isacchi; Paolo Sarmientos, all of Milan; Gilles Cauet, Buccinasco, all of Italy

[73] Assignee: Farmitalia Carlo Erba S.R.L., Milan, Italy

[21] Appl. No.: 71,046

[22] Filed: Jun. 2, 1993

Related U.S. Application Data

[63] Continuation of Ser. No. 863,549, Apr. 6, 1992, abandoned, which is a continuation of Ser. No. 466,441, Jul. 16, 1990, abandoned.

[30] Foreign Application Priority Data

Sep. 16, 1988 [GB] United Kingdom ............ 8821795.5

[51] Int. Cl.$^5$ ........................ C12N 15/00; C12N 1/20; C12P 21/00; A61K 37/36
[52] U.S. Cl. .................................. 435/69.4; 530/399; 435/252.33
[58] Field of Search ............ 530/399; 435/69.4, 252.3, 435/252.33, 320.1; 514/12; 536/23.5, 23.51

[56] References Cited

U.S. PATENT DOCUMENTS

| | | | |
|---|---|---|---|
| 4,994,559 | 2/1991 | Mascatelli et al. | 530/399 |
| 5,026,839 | 6/1991 | Mascatelli et al. | 536/27 |

FOREIGN PATENT DOCUMENTS

| | | |
|---|---|---|
| 0237966 | 9/1987 | European Pat. Off. . |
| 0275204 | 7/1988 | European Pat. Off. . |
| 0281822 | 9/1988 | European Pat. Off. . |
| 0326907 | 8/1989 | European Pat. Off. . |
| WO92/08373 | 5/1992 | PCT Int'l Appl. . |
| 2245831 | 1/1992 | United Kingdom . |

OTHER PUBLICATIONS

Nagai, K. et al., *Nature*, 309: 810-812, 1984.
Dialog Information Services, File 154, Medline 82-89, Dialog accession No. 88162887, Seno M. et al.: "Stabilizing fibroblast growth factor using protein engineering", Biochem Res Commun Mar. 15, 1988, 151 (2) pp. 701-708.
Dialog Information Services File 55, Biosis, Biosis No. 87037476, Fox G. M. et al.: "Production biological activity and structure of recombinant basic fibroblast growth factor and an analog with cysteine replaced by serine", J. Biol Chem. 263 (34) 1988, 18452-18453.

*Primary Examiner*—Robert J. Hill, Jr.
*Assistant Examiner*—Marianne Porta Allen
*Attorney, Agent, or Firm*—Oblon, Spivak, McClelland, Maier & Neustadt

[57] ABSTRACT

The present invention relates to the production, by recombinant DNA techniques, of derivatives of basic fibroblast growth factor (bFGF). These derivatives of bFGF can act as antagonists and/or superagonists of the wild type molecule in the angiogenic process. These derivatives, as well as wild type bFGF, may be prepared by the use of strains or *E. coli* which have been transformed with plasmids carrying nucleotide sequence coding for human and bovine bFGF and their derivatives.

3 Claims, 9 Drawing Sheets

Met Ala Ala Gly Ser Ile Thr Thr Leu Pro Ala Leu Pro Glu
1                                        10

Asp Gly Gly Ser Gly Ala Phe Pro Pro Gly His Phe Lys Asp
                    20

Pro Lys Arg Leu Tyr Cys Lys Asn Gly Gly Phe Phe Leu Arg
        30                              40

Ile His Pro Asp Gly Arg Val Asp Gly Val Arg Glu Lys Ser
                        50

Asp Pro His Ile Lys Leu Gln Leu Gln Ala Glu Glu Arg Gly
            60                                      70

Val Val Ser Ile Lys Gly Val Cys Ala Asn Arg Tyr Leu Ala
                                80

Met Lys Glu Asp Gly Arg Leu Leu Ala Ser Lys Cys Val Thr
                90

Asp Glu Cys Phe Phe Phe Glu Arg Leu Glu Ser Asn Asn Tyr
100                                         110

Asn Thr Tyr Arg Ser Arg Lys Tyr Thr Ser Trp Tyr Val Ala
                        120 Ser

Leu Lys Arg Thr Gly Gln Tyr Lys Leu Gly Ser Lys Thr Gly
            130                             Pro

Pro Gly Gln Lys Ala Ile Leu Phe Leu Pro Met Ser Ala Lys
                                        150

Ser
155                     *FIG. 2*

```
              1                                          10                                      20
hst    Met Ser Gly Pro Gly Thr Ala Ala Val Ala Leu Leu Pro Ala Val Leu Leu Ala Leu Leu
                                         30                                      40
hst    Ala Pro Trp Ala Gly Arg Gly Gly Ala Ala Ala Pro Thr Ala Pro Asn Gly Thr Leu Glu
int-2                                                                           Met Gly
                                         50                                      60
hst    Ala Glu Leu Glu Arg Arg Trp Glu Ser Leu Val Ala Leu Ser Leu Ala Arg Leu Pro Val
hBFGF                                                                       Met Ala Ala Gly Ser
int-2  Leu Ile Trp Leu Leu Leu Ser Leu Leu Glu Pro Ser Trp Pro Thr Thr Gly Pro Gly
                                         70
hst    Ala Ala Gln Pro Lys Glu Ala Ala Val Gln Ser Gly Ala Gly Asp Tyr Leu Leu Gly
hBFGF  Ile Thr Thr Leu Pro Ala Leu Pro Glu Asp Gly Gly Ser Gly Ala Phe Pro Pro Gly His
hAFGF                                                               Phe Asn Leu Pro Gly Asn
int-2  Thr Arg Leu Arg Arg Asp Ala Gly Gly Arg Gly Gly Val Tyr Glu His Leu Gly Gly
                         80                                      90
hst    Ile Lys Arg Leu Arg Arg Leu Tyr Cys Asn Val Gly Ile Gly Phe His Leu Gln Ala Leu
hBFGF  Phe Lys Asp Pro Lys Arg Leu Tyr Cys Lys Asn Gly     Gly Phe Phe Leu Arg Ile His
hAFGF  Tyr Lys Lys Pro Lys Leu Leu Tyr Cys Ser Asn Gly     Gly His Phe Leu Arg Ile Leu
int-2  Ala Pro Arg Arg Arg Lys Leu Tyr Cys     Ala Thr Lys Tyr His Leu Gln Leu His
                                         110
hst    Pro Asp Gly Arg Ile Gly Gly Ala His Ala Asp Thr Arg Asp Ser Leu     Leu Glu Leu
hBFGF  Pro Asp Gly Arg Val Asp Gly Val Arg Glu Lys Ser Asp Pro His Ile Lys Leu Gln Leu
hAFGF  Pro Asp Gly Thr Val Asp Gly Thr Arg Asp Arg Ser Asp Gln His Ile Gln Leu Gln Leu
int-2  Pro Ser Gly Arg Val Asn Gly Ser Leu Glu Asn Ser Ala Tyr Ser Ile     Leu Glu Ile
```

FIG. 3A

FIG. 3B

FIG. 4A  FIG. 4B  FIG. 4C  FIG. 4D  FIG. 4E  FIG. 4F  FIG. 4G

FIG. 5A

|         |     |     |     |     |     |     |     |     |     |     | 100 |     |     |     |     |     |     |     |     | 110 |     |     |     |     |     |     |     |     |     | 120 |     |     |     |
|---------|-----|-----|-----|-----|-----|-----|-----|-----|-----|-----|-----|-----|-----|-----|-----|-----|-----|-----|-----|-----|-----|-----|-----|-----|-----|-----|-----|-----|-----|-----|-----|-----|-----|
| bFGF WT | Ser | Lys | Cys | Val | Thr | Asp | Glu | Cys | Phe | Phe | Phe | Glu | Arg | Leu | Glu | Ser | Asn | Asn | Tyr | Asn | Thr | Tyr | Arg | Ser | Arg | Lys | Tyr | Thr | Ser | Trp | Tyr |
| Mi-bFGF | Ser | Lys | Cys | Val | Thr | Asp | Glu | Cys | Phe | Phe | Phe | Glu | Arg | Leu | Glu | Ser | Asn | Asn | Tyr | Asn | Thr | Tyr | Arg | Ser | Arg | Lys | Tyr | Thr | Ser | Trp | Tyr |
| M2-bFGF | Ser | Lys | Cys | Val | Thr | Asp | Glu | Cys | Phe | Phe | Phe | Glu | Arg | Leu | Glu | Ser | Asn | Asn | Tyr | Asn | Thr | Tyr | Arg | Ser | Arg | Lys | Tyr | Thr | Ser | Trp | Tyr |
| M3-bFGF | Ser | Lys | Cys | Val | Thr | Asp | Glu | Cys | Phe | Phe | Phe | Glu | Arg | Leu | Glu | Ser | Asn | Asn | Tyr | Asn | Thr | Tyr | Arg | Ser | Arg | Lys | Tyr | Thr | Ser | Trp | Tyr |
| M4-bFGF | Ser | Lys | Cys | Val | Thr | Asp | Glu | Cys | Phe | Phe | Phe | Glu | Arg | Leu | Glu | Ser | Asn | Asn | Tyr | Asn | Thr | Tyr | Arg | Ser | Arg | Lys | Tyr | Thr | Ser | Trp | Tyr |
| M5-bFGF | Ser | Lys | Cys | Val | Thr | Asp | Glu | Cys | Phe | Phe | Phe | Glu | Arg | Leu | Glu | Ser |  -  |  -  |  -  |  -  |  -  |  -  |  -  |  -  |  -  |  -  |  -  | Thr | Ser | Trp | Tyr |
| M6a-bFGF| Ser | Lys | Cys | Val | Thr | Asp | Glu | Cys | Phe | Phe | Phe | Glu | Arg | Leu | Glu | Ser | Asn | Asn | Tyr | Asn | Thr | Tyr | Arg | Ser | Arg | Lys | Tyr | Thr | Ser | Trp | Tyr |
| M6b-bFGF| Ser | Lys | Cys | Val | Thr | Asp | Glu | Cys | Phe | Phe | Phe | Glu | Arg | Leu | Glu | Ser | Asn | Asn | Tyr | Asn | Thr | Tyr | Arg | Ser | Gln | Gln | Tyr | Thr | Ser | Trp | Tyr |
|         |     |     |     |     |     |     |     |     |     |     |     |     |     |     |     |     |     |     |     |     |     |     |     |     |     |  *  |  *  |     |     |     |     |

|         |     |     |     |     |     |     | 130 |     |     |     |     |     |     |     |     |     | 140 |     |     |     |     |     |     |     |     |     | 150 |     |     |     |     |     |
|---------|-----|-----|-----|-----|-----|-----|-----|-----|-----|-----|-----|-----|-----|-----|-----|-----|-----|-----|-----|-----|-----|-----|-----|-----|-----|-----|-----|-----|-----|-----|-----|-----|
| bFGF WT | Val | Ala | Leu | Lys | Arg | Thr | Gly | Gln | Tyr | Lys | Leu | Gly | Ser | Lys | Thr | Gly | Pro | Gly | Gln | Lys | Ala | Ile | Leu | Phe | Leu | Pro | Met | Ser | Ala | Lys | Ser |
| Mi-bFGF | Val | Ala | Leu | Lys | Arg | Thr | Gly | Gln | Tyr | Lys | Leu | Gly | Ser | Lys | Thr | Gly | Pro | Gly | Gln | Lys | Ala | Ile | Leu | Phe | Leu | Pro | Met | Ser | Ala | Lys | Ser |
| M2-bFGF | Val | Ala | Leu | Lys | Arg | Thr | Gly | Gln | Tyr | Lys | Leu | Gly | Ser | Lys | Thr | Gly | Pro | Gly | Gln | Lys | Ala | Ile | Leu | Phe | Leu | Pro | Met | Ser | Ala | Lys | Ser |
| M3-bFGF | Val | Ala | Leu | Lys | Arg | Thr | Gly | Gln | Tyr | Lys | Leu | Gly | Ser | Lys | Thr | Gly | Pro | Gly | Gln | Lys | Ala | Ile | Leu | Phe | Leu | Pro | Met | Ser | Ala | Lys | Ser |
| M4-bFGF | Val | Ala | Leu | Lys | Arg | Thr | Gly | Gln | Tyr | Lys | Leu | Gly | Ser | Lys | Thr | Gly | Pro | Gly | Gln | Lys | Ala | Ile | Leu | Phe | Leu | Pro | Met | Ser | Ala | Lys | Ser |
| M5-bFGF | Val | Ala | Leu | Lys | Arg | Thr | Gly | Gln | Tyr | Lys | Leu | Gly | Ser | Lys | Thr | Gly | Pro | Gly | Gln | Lys | Ala | Ile | Leu | Phe | Leu | Pro | Met | Ser | Ala | Lys | Ser |
| M6a-bFGF| Val | Ala | Leu | Gln | Gln | Thr | Gly | Gln | Tyr | Lys | Leu | Gly | Ser | Lys | Thr | Gly | Pro | Gly | Gln | Lys | Ala | Ile | Leu | Phe | Leu | Pro | Met | Ser | Ala | Lys | Ser |
| M6b-bFGF| Val | Ala | Leu | Gln | Gln | Thr | Gly | Gln | Tyr | Lys | Leu | Gly | Ser | Lys | Thr | Gly | Pro | Gly | Gln | Lys | Ala | Ile | Leu | Phe | Leu | Pro | Met | Ser | Ala | Lys | Ser |
|         |     |     |     |  *  |  *  |     |     |     |     |     |     |     |     |     |     |     |     |     |     |     |     |     |     |     |     |     |     |     |     |     |     |

FIG. 5B

```
 *   *   *   *   *   *   *   *   *   *   *   *   *   *
ATG GCT GCT GGT TCT ATC ACT ACT CTG CCG GCT CTG CCG GAA
 *   *   *   *   *   *
GAC GGT GGT TCT GGT GCT TTC CCG CCC GGC CAC TTC AAG GAC

CCC AAG CGG CTG TAC TGC AAA AAC GGG GGC TTC TTC CTG CGC

ATC CAC CCC GAC GGC CGA GTT GAC GGG GTC CGG GAG AAG AGC

GAC CCT CAC ATC AAG CTA CAA CTT CAA GCA GAA GAG AGA GGA

GTT GTG TCT ATC AAA GGA GTG TGT GCT AAC CGT TAC CTG GCT

ATG AAG GAA GAT GGA AGA TTA CTG GCT TCT AAA TGT GTT ACG

GAT GAG TGT TTC TTT TTT GAA CGA TTG GAA TCT AAT AAC TAC

AAT ACT TAC CGG TCA AGG AAA TAC ACC AGT TGG TAT GTG GCA
                                    TCC
TTG AAA CGA ACT GGG CAG TAT AAA CTT GGA TCC AAA ACA GGA
                                        CCC
CCT GGG CAG AAA GCT ATA CTT TTT CTT CCA ATG TCT GCT AAG

AGC
```

*FIG. 6*

DELETION MUTANT OF BASIC FIBROBLAST GROWTH FACTOR AND PRODUCTION THEREOF

This application is a continuation of application Ser. No. 07/863,549, filed on Apr. 6, 1992, which is a continuation of application Ser. No. 07/466,441, filed on Jul. 16, 1990, both now abandoned.

The present invention relates to new molecular entity derivatives of basic fibroblast growth factor (bFGF) to their production by recombinant DNA techniques, as well as to related expression plasmids and DNA coding sequences. The new molecular bFGF variants of the invention can act as antagonists and/or superagonists of the wild type molecule in the angiogenic process.

The procedure disclosed within the text of the present invention for the production of these new molecules, as well as of wild type bFGF, is based on recombinant strains of E. coli which have been transformed with plasmids carrying nucleotide sequences coding for human and bovine bFGF and their derivatives.

INTRODUCTION

The formation of blood capillaries occurs in a number of important biological processes, either physiological, such as organ development and wound healing, or pathological, such as tumor growth (Denekamp J: Vascular endothelium as the vulnerable element in tumors. Acta Radiol. (oncol) 23 p. 217-225, 1984; Hobson B and Denekamp J: Endothelial proliferation in tumours and normal tissues: continous labelling studies. Br.J. Cancer 49 p. 405-413, 1984; Folkman J: Tumor angiogenesis, Adv. Cancer Res. 43 p. 175-203, 1985).

While the sequence of events leading to neovascularization has been characterized morphologically, the molecular mechanisms by which this process occurs are still poorly understood. The control of growth in the capillary endothelium appears to be a very tight one, since these cells normally form a static monolayer whose proliferation is triggered in the angiogenic process (Folkman J: Tumor angiogenesis, Adv. Cancer Res. 43 p. 175-203, 1985; Joseph-Silverstein J. and Rifkin B. D.: Endothelial cell growth factors and the vessel wall, Seminars in Thromb. and Hemost. 13 p. 504-513, 1987).

The normally quiescent nature of the endothelial cells may be explained in part by the apparent lack of endothelial cell growth factors in plasma.

The major endothelial cell mitogens in fact, are not found in plasma, although they are present in extracts of almost all tissues studied and in many normal and tumor cell lines as well (Joseph-Silverstein J. and Rifkin B. D.: Endothelial cell growth factors and the vessel wall, Seminars in Thromb. and Hemost. 13 p. 504-513, 1987; Folkman J; and Klagsbrun M.: Angiogenic Factors, Science, 235 p. 442-447, 1987).

Therefore, the localized induction of rapid endothelial cell proliferation may involve the release of endothelial cell mitogens from cells in response to environmental cues.

The best characterized of the endothelial cell mitogens are a family of polypeptide growth factors, including basic fibroblast growth factor (bFGF), also known as heparin-binding growth factors for their high affinity to heparin (Thomas K.: Fibroblast growth factors, FASEB J., 1 p. 434-440, 1987; Gospodarowicz D., Neufeld G, and Schweigerer L.: Fibroblast growth factor: structural and biological properties, J. Cell. Physiol., 5 p. 15-26, 1987).

Basic FGF has been purified from most mesoderm- or neuroectoderm- derived tissues or cells.

Structural studies have shown that bFGF is a single chain polypeptide made of 146 amino acids, which can also exist in $NH_2$-terminally truncated forms missing the first 10-20 amino acids.

The truncated forms of FGF are as potent as native bFGF as demonstrated by radioreceptor binding and biological assays (Gospodarowicz D., Neufeld G. and Schweigerer L.: Fibroblast growth factor, Mol. Cell. Endocrin. 46 p. 187-206, 1986; Gospodarowicz D., Neufeld G. and Schweigerer L.: Molecular and biological characterization of fibroblast growth factor: an angiogenic factor which also controls the proliferation and differentiation of mesoderm and neuroectoderm derived cells., Cell. Differ., 19 p. 1-17, 1986; Thomas K. and Gimenez-Gallego G.: Fibroblast growth factors: broad spectrum mitogens with potent angiogenic activity. Trends Biochem. Sci. 11 p. 81-84, 1986).

In addition, modifications of the purification protocols by substitution of neutral for acidic extraction from homogeneized tissue and inclusion of protease inhibitors have yielded a longer 154-residue form (Ueno N., Baird A., Esch F., Ling N. and Guillemin R.: Isolation of an amino terminal extended form of basic fibroblast growth factor. Biochem. Biophys. Res. Commun., 138 p. 580-588, 1986; Story M. T. Esch. F., Shimasaki S., Sasse J., Jacobs S. C. and Lawson R. K.: Aminoterminal sequence of a large form of basic fibroblast growth factor isolated from human benign prostatic hyperplastic tissue. Biochem Biophys.Res.Commun. 142, p. 702-709, 1987; Klagsbrun M., Smith S., Sullivan R. SHing Y., Davidson S., Smith J. A. and Sasse J.: Multiple forms of basic fibroblast growth factor: amino-terminal cleavages by tumor cell and brain cell-derived acid proteinases. Proc. Natl. Acad. Sci. USA 84 p. 1839-1843, 1987).

The observed microheterogeneity of FGFs seems to be due, at least in part, to partial proteolysis near the amino termini that occurs either in vivo or during purification. However, because the various forms appear to be equally active, the microheterogeneity is probably physiologically irrelevant.

Basic FGF seems to have been extremely well conserved through evolution. For example, bovine and human bFGF differ in only two of their 146 amino acids, giving an overall amino acid sequence homology of 98.7% (Gospodarowicz D., Neufeld G. and Schweigerer L.: Molecular and biological characterization of fibroblast growth factor: an angiogenic factor which also controls the proliferation and differentiation of mesoderm and neuroectoderm derived cells., Cell. Differ., 19 p. 1-17, 1986).

Related to bFGF is acidic FGF (aFGF), which shares a 55% total sequence homology with bFGF. Acidic FGF is a 140-amino acid polypeptide that can also exist in an $NH_2$-terminally truncated form missing the first 6 amino acids (Gimenez-Gallego G., Conn G., Hatcher V. B. and Thomas K. A.: The complete amino acid sequence of human brain-derived acidic fibroblast growth factor. Biochem. Biophys.Res.Commun. 138, p. 611-617, 1986).

Basic FGF and acidic FGF possess two potential binding domains for heparin, one located near their $NH_2$ terminus, the other near the COOH-terminus. Both domains could be involved in the strong affinity of FGF toward heparin (Gospodarowicz D., Neufeld G. and Schweigerer L.: Fibroblast growth factor, Mol. Cell. Endocrin. 46 p. 187-206, 1986; Gospodarowicz D., Neufeld G. and Schweigerer L.: Molecular and biological characterization of fibroblast growth factor: an angiogenic factor which also controls the proliferation and differentiation of mesoderm and neuroectoderm derived cells., Cell. Differ., 19 p. 1-17, 1986; Baird A., Schubert D., Ling N., and Guillemin R., Receptor- and heparin-binding domains of basic fibroblast growth factor Proc. Natl. Acad. Sci. U.S.A. 85, p. 2324-2328, 1988).

The high degree of homology between aFGF and bFGF suggests that they are derived from a single ancestral gene. Recently, the FGF genes have been cloned and complementary DNA sequences of both bFGF and aFGF have been determined (Abraham J. A. Whang J. L. Tumolo A., Mergia A., Friedman J., Gospodarowicz D. and Fiddes J. C.: Human basic fibroblast growth factor: nucleotide sequence and genomic organization. EMBO J., 5 p. 2523-2528, 1986; Abraham J. A., Mergia A., Whang J. L. Tumolo A., Friedman J., Hjerrild K. A., Gospodarowicz D. and Fiddes J. C.: Nucleotide sequence of a bovine clone encoding the angiogenic protein, basic fibroblast growth factor. Science 233, p 545-548, 1986; Jaye M., Howk R., Burgess G. A., Ricca W., Chiu I. M., Ravera M. W., O'Brien S. J., Modi W. S., Maciag T. and Drolian W. N.: Human endothelial cell growth factor: Cloning nucleotide sequence and chromosome localization. Science 233, p. 541-545, 1986).

Analysis of the nucleotide sequence of human and bovine cDNA clones suggests that the primary translation product for basic FGF is composed of 155 amino acids. However, recently Sommer et al. have isolated a new 157-amino acid form of human basic FGF with two extra amino acids at the $NH_2$-terminus (Sommer A., Brewer M. T., Thompson R. C., Moscatelli D., Presta M. and rifkin D. B.: A form of human basic fibroblast growth factor with an extended amino terminus. Biochem Biophys. Res. Commun., 144 p. 543-550, 1987). Interestingly, these two amino acids correspond to the codons found in the previously described human cDNA clone. FIG. 1 summarizes the different forms of basic FGF isolated to date or deduced by the cDNA sequence. FIG. 2 shows the primary structure of the 155 amino acids form.

As mentioned above, the present invention relates to molecular variants of human basic FGF. These new molecular entities, never found in nature before, have been obtained by site-directed mutagenesis of the gene coding for the 155-amino acids form.

However, the microheterogeneity of the amino-terminus of the basic FGFs and its physiological irrelevance indicate that the modifications, disclosed and described in the present invention for the 155 amino acid form, are equivalent to the same ones possibly obtained on other forms of FGF (see below).

BACKGROUND OF THE INVENTION

As already pointed out, angiogenesis is a tightly controlled process which can assume a pathological significance for it contributes to the development of solid tumors. In view of the key role of bFGF in angiogenesis, variants of this molecule which can compete with endogenous FGF while being biologically inactive could be valuable tools in the anticancer therapy.

On the other hand, new capillary growth is at the basis of normal homeostatic mechanisms that underlie reproduction, growth and development. Consequently, analogues of bFGF with increased biological activity could span a number of potential applications such as healing burns, wounds (including corneal) and surgical incisions; treating skin ulcers, including bedsores; restarting blood flow after heart attacks by revascularizing the damaged tissue; and treating some musculoskeletal injures.

The object of the present invention is therefore the design and production of recombinant analogues of basic FGF that have modified biological activity.

In order to understand which changes in the amino acids sequence of basic FGF could affect its functional properties, a number of related proteins which have a very high homology with basic FGF can be considered. This family of proteins includes acidic FGF as well as hst and int-2, two oncogene products recently discovered (Yoshida T., Miyagawa K., Odagiri H., Sakamoto H., Little P. F. R., Terada M. and Sugimura T.: Genomic sequence of hst, a transforming gene encoding a protein homologous to fibroblast growth factors and the int-2-encoded protein. Proc. Natl. Acad. Sci. USA. 84 p. 7305-7309, 1987; Delli Bovi P., Curatola A. M., Kern F. G., Greco A., Ittmann M. and Basilico C.: An oncogene isolated by transfection of kaposi's sarcoma DNA encodes a growth factor that is a member of the FGF family. Cell 50 p. 729-737, 1987).

All these molecules, including bFGF, constitute a family of factors involved in cell growth and regulation. The primary sequence of these proteins is compared in FIG. 3.

When the homology between these proteins is considered, highly conserved regions in the primary structure can be observed. Conservation of such domains may signify not only structural, but also some functional homology among these proteins.

Indeed, all these proteins share a strong affinity for heparin and seem to play an important role in the angiogenic processes, possibly including new capillary proliferation supporting tumor development.

If the conserved domains may be responsible for the common characteristics of these proteins, the highly diversified sequences may account for the different biological role of these factors. Consequently, alterations in either of these regions may dramatically affect the biological activity of basic FGF.

In view of these considerations, the authors of the present invention have constructed, by genetic engineering techniques, new derivatives of human and bovine basic FGF which, in one case, have lost amino acid sequences within different regions of the bFGF molecule and, in a second case, have amino acid substitutions in specific positions. The modifications were chosen according to homologies and differences among several known growth factors. The molecular characteristics of the mutants are described below.

Analogues can be Obtained as Recombinant Proteins in a Selected Expression System The desired changes can be achieved modifying, by genetic engineering techniques, the bFGF gene prior to its expression in a suitable organism. By bFGF gene it is meant a DNA sequence that can be obtained by cloning from a cDNA library or by assembling synthetic oligonucleotides (Maniatis T., Frisch E. F. and Sambrook J.: Molecular cloning. A laboratory manual. Cold Spring Harbour Laboratory. Cold Spring Harbour, N.Y., 1982).

The invention concerns also a recombinant DNA method for the production of bFGF and its derivatives.

Molecular Characteristics of the Mutants

In the present invention, by 'analogues', 'mutants' or 'derivatives' it is meant molecules of bFGF with altered amino acid sequence. All the natural forms of bFGF isolated to date and described in the introduction, can be altered to obtain equivalent analogues. Preferred analogues are mutants of the 155 amino acids form. Both the human and the bovine sequence have been modified in the present invention. The new bFGF derivatives were constructed by oligonucleotide-directed mutagenesis.

In particular, oligonucleotides were designed and synthesized to cause deletions of coding regions within the human and bovine bFGF genes. The mutagenesis technique used to obtain the mutants is described in detail in the "Methods" section.

The mutated genes are then inserted in E. coli expression vectors which can direct the synthesis of the new bFGF derivatives. The recombinant molecules are then purified, characterized and ultimately produced in large amounts.

The new bFGF derivatives, constituting the object of the present invention, are described in detail hereafter and generally illustrated in FIG. 4. Numbering of the amino acids corresponds to the 155 residues form, a methionine being residue number 1 and a serine being residue 155. However, all the described forms of bFGF can be changed to obtain the same deletions. Moreover, both the bovine and the human form can be used for the construction of the mutants.

Preferred bFGF derivatives are the following:

M1-bFGF is a derivatives of bFGF lacking residues 27 through 32 (Lys-Asp-Pro-Lys-Arg-Leu) of the amino acid sequence;

M2-bFGF is a derivative of bFGF lacking residues 54 through 58 (Glu-Lys-Ser-Asp-Pro) of the amino acid sequence;

M3-bFGF is a derivative of bFGF lacking residues 70 through 75 (Gly-Val-Val-Ser-Ile-Lys) of the amino acid sequence;

M4-bFGF is a derivative of bFGF lacking residue 78 through 83 (Cys-Ala-Asn-Arg-Tyr-Leu) of the amino acid sequence;

M5-bFGF is a derivative of bFGF lacking residues 110 through 120 (Asn-Asn-Tyr-Asn-Thr-Tyr-Arg-Ser-Arg-Lys-Tyr) of the amino acid sequence;

M6a-bFGF is a derivative of bFGF where the lysine and arginine residues respectively in positions 128 and 129 are replaced by glutamine residues;

M6b-bFGF is a derivative of bFGF where the lysine residues in positions 119 and 128 and the arginine residues in positions 118 and 129 are all replaced by glutamine residues.

The detailed amino acid sequence of the mutants is illustrated in FIG. 5.

Polypeptides with additional amino acid residues added to either the NH$_2$ or the COOH terminus, or to both, are considered within the present invention. Such extentions may be necessary for technical reasons in the expression of the mutants by recombinant DNA techniques (Courtney M., Jallat S., Tessier L. H. Benavente A. and Crystal R. G.: Synthesis in E. coli of alfa1-antitrypsin variants of therapeutic potential for emphysema and thrombosis. Nature, 313, p. 149–151, 1985; Nagai K. and Thogersen H. C.: Generation of β-globin by sequence specific proteolysis of a hybrid protein produced in E. coli. Nature, 309, p. 810–812, 1984).

Alternatively, the additional residues may serve to enhance the pharmacological efficacy of the mutants, for example by prolonging their circulating half life in plasma.

Details of the procedure developed for the production of the mutants.

In order to efficiently produce the new bFGF derivatives, we have developed a recombinant DNA procedure which allows the preparation, at the laboratory and pilot scales, of the necessary quantities for a biological and clinical evaluation of the different molecules.

This procedure is based on the fermentation of strains of E. coli modified by genetic engineering techniques so as to express, at high levels, the mutated genes.

Details of the production procedure are here indicated:

1) Construction of a synthetic DNA sequence for bFGF

All the sequences used for the expression of wild type basic FGF and its derivatives were synthetically reconstructed. This was accomplished by synthesizing oligonucleotides with overlapping sequences on an automatic DNA synthesizer, such as Applied Biosystem Inc. 380B model (Caruthers M. H.: Gene synthesis machines; DNA chemistry and its uses. Science, 230, p. 281–285, 1985).

The overlapping oligonucleotides were joined to form a double stranded DNA chain, gaps being filled in with DNA polymerase and with T4 ligase.

Immediately at 5' of the FGF-encoding sequence in the sense strand there was provided an ATG start signal. In the case of 155 amino acids form of bFGF we could use as starting codon the ATG coding for a methionine naturally occurring as first residue, so that no extra amino acids are added to the N-terminus of the expressed polypeptide (Abraham J. A., Whang J. L., Tumolo A., Mergia A., Friedman J., Gospodarowicz D. and Fiddes J. C.: Human basic fibroblast growth factor: nucleotide sequence and genomic organization. EMBO J., 5 p. 2523–2528, 1986; Abraham J. A. Mergia A., Whang J. L., Tumolo A., Friedman J., Hjerrild K. A., Gospodarowicz D. and Fiddes J. C.: Nucleotide sequence of a bovine clone encoding the angiogenic protein, basic fibroblast growth factor. Science 233, p 545–548, 1986). Alternatively, to increase the expression of FGF in E. coli its 5'-end sequence was changed without altering the primary structure of the protein. More particularly, the nucleotide sequence was modified as illustrated in FIG. 6.

2) Construction of the mutated sequences for bFGF derivatives To obtain the mutants described in the present invention, the wild type bFGF sequence was changed in order to achieve the desired deletions. This was achieved modifying the gene by site directed mutagenesis (Norris K., Norris F., Christiansen L. and Fiil N.: Efficient site-directed mutagenesis by simultaneous use of two primers, Nucleic Acid Research, 11, 5103–5112, 1983).

The principle of this method is to subclone the bFGF gene into a vector which can be obtained in a single strand form such as the phage vector M13. The recombinant single strand is annealed with a complementary synthetic oligodeoxyribonucleotide coding for the desired modifications. DNA polymerase and ligase are then used to extend the new strand and to ligate it into a circular form. The newly created heteroduplex DNA is used to transform a cell line into which it can replicate and yield a progeny where the phage bearing the wild type gene or the gene with the desired deletion will segregate in two different molecular species.

The starting mutagenic oligonucleotides can then be used as probes to recognize the mutated genes. The site-directed mutagenesis technique is described in detail in the Methods' section.

In particular, the synthetic sequence for wild type bFGF, alternatively bovine or human, was inserted in an M13 vector and the resulting single strand used as mutagenesis template (Norris K.; Norris F., Christiansen L. and Fiil N.: Efficient site-directed mutagenesis by simultaneous use of two primers, Nucleic Acid Research, 11, 5103–5112, 1983).

3) Expression of the wild type bFGF and of its derivatives

To obtain the expression of the wild type and mutated sequences of bFGF in recombinant strains of *E. coli* these sequences were inserted in expression plasmids harbouring the sequences responsible for transcription and translation of the new genes. More particularly, we have used as regulatory signals the tryptophan promoter of *E. coli* and the ribosome binding site region of the lambda CII protein (Hendrix R. W., Roberts J. W., Stahl F. W. and Weisberg R. A.: Lambda II Cold Spring Harbour Laboratory, Cold Spring Harbour, N.Y. 1983).

The promoter Ptrp was obtained from the commercially available plasmid pDR720 (Pharmacia). The Shine-Dalgarno CII sequence was obtained by chemical synthesis according to the published sequence (Hendrix R. W., Roberts J. W., Stahl F. W., and Weisberg R. A.: Lambda II Cold Spring Harbour Laboratory, Cold Spring Harbour, N.Y. 1983).

Figure 7:
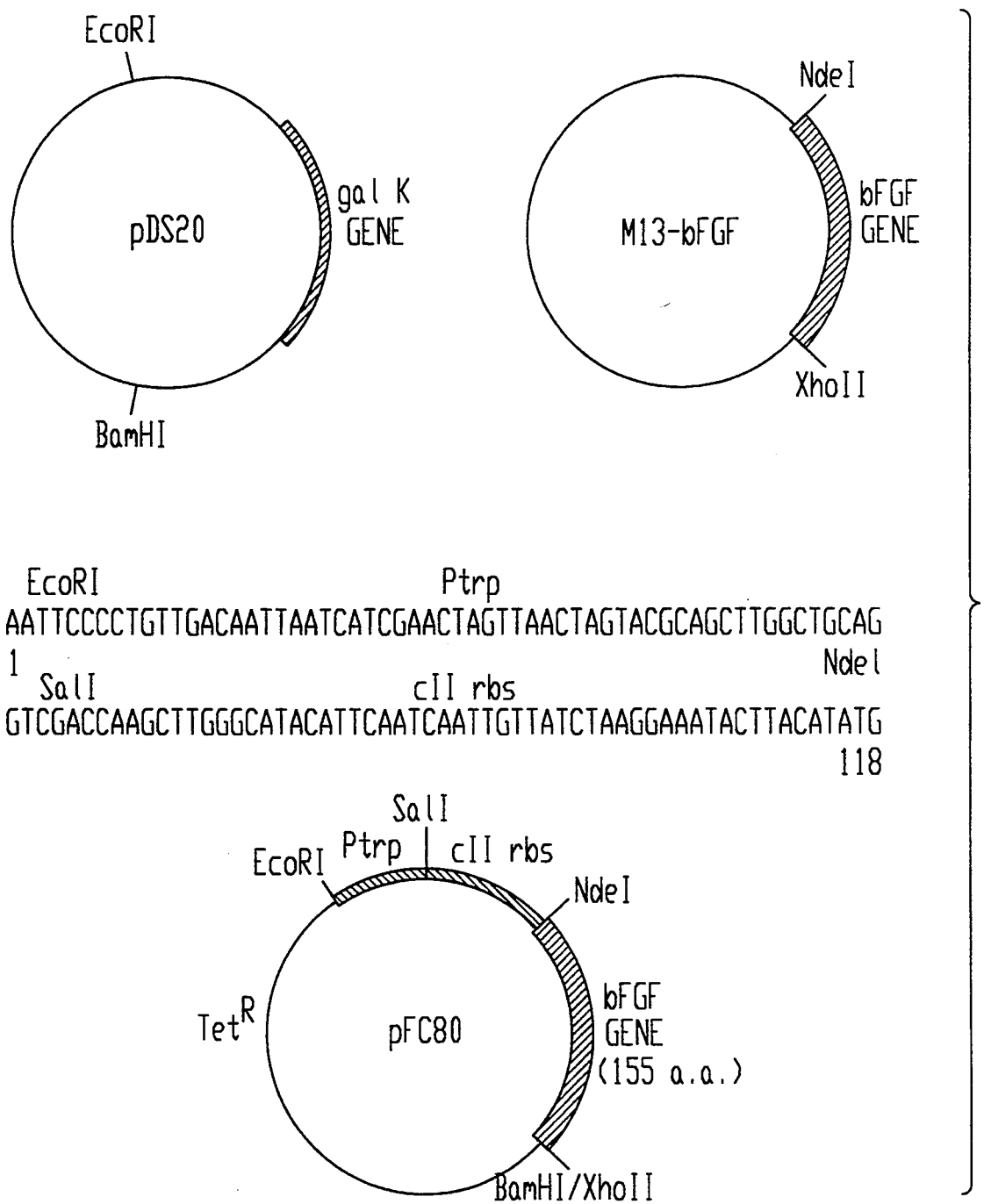

A typical expression vector for the wild type bFGF and its derivatives is illustrated in FIG. 7. More particularly, it was constructed by assembling the following fragments:

a) the large Eco RI-Bam HI fragment of plasmid pDS20 (Duester G., Elford R. M., Holmes W. N.: Fusion of the Escherichia coli leucyl transfer RNA-I promoter to the gal-K gene. Analysis of sequences necessary for growth rate dependent regulation Cell 30, p. 855–964, 1982)

b) an Eco RI-Sal I fragment from plasmid pDR720 (Pharmacia, Sweden), carrying the tryptophan promoter;

c) a synthetic Sal I-Nde I oligonucleotide coding for the cII ribosome binding site;

d) a sinthetic Nde I-Xho II (Bam HI-compatible) fragment harbouring the wild type or mutated sequence for bFGF and its derivatives.

A preferred sequence for wild type bFGF is reported in FIG. 6 Preferred sequences for bFGF analogues are modifications of this sequence according to the mutations shown in FIG. 5.

Induction of expression of the new genes and analysis of the resulting recombinant proteins were performed as described in the 'Methods' session.

4) Purification of the recombinant molecules and biological assays

The recombinant mutants can be purifed from bacterial lysates and tested for their biological characteristics in comparison with the wild type bFGF.

A typical purification process is the following: cells are disrupted by sonication, centrifuged and the supernatant is applied on a ion-exchange S-Sepharose column.

The protein is eluted with a sodium chloride gradient and directly loaded on a heparin-Sepharose affinity column.

The protein is eluted with a sodium chloride gradient and desalted by gel filtration before lyophilization. Purified analogues can be subsequently tested for their biological activity.

Properties of the mutants, their utility and administration

The new molecules of the present invention can act as antagonists and/or superagonists of the wild-type bFGF molecule.

The bFGF agonistic activity was evaluated, for example, on the basis of the capability of increasing proliferation of endothelial cells according to a test procedure analogous to that described by Presta et al in Molecular and Cellular Biol. 6, p. 4060, 1986.

The bFGF antagonistic activity was evaluated, e.g., on the basis of the inhibition of the binding of $^{125}$I-bFGF according to a test procedure analogous to that described by Baird et al in Proc. Notl. Acad. Sci. USA, 85, p. 2324, 1988.

Thus, for example, the compound of the invention identified by the abbreviation M6b was found to produce 50% increase of endothelial cell proliferation at the dose of 1 ng/ml, which is indicative of a particularly appreciable b-FGF agonistic activity.

Again as example, the compounds of the invention identified as M3-bFGF and M6a were found to produce about 20% and, respectively, about 70% inhibition of binding of $^{125}$I-bFGF(3 ng/ml) in the presence of 300 ng/ml of mutant, which is indicative of bFGF antagonistic activity.

As bFGF superagonists the compounds of the invention can act as promoters of vascularization, cell growth or cell survival, and, therefore, find application in, e.g., tissue repair, for instance healing of wounds, burns, bone fractures, surgical abrasions, ulcers, including tissue repair during ischaemia and miocardial infarction.

As antagonists of bFGF, the compounds of the invention may act as angiogenesis inhibitors and be, therefore, useful for, e.g., the treatment of diseases where neovascularization is a dominant patology, e.g. retinopathies of the eye; neovascular glaucoma; skin disorders such as, e.g., psoriasis; chronic inflammation; rheumatoid arthritis; as well as, as already mentioned before, in the treatment of certain neoplasms, particularly angiogenic neoplasms, as a valuable tool for inhibiting tumoral angiogenesis.

The compounds of the invention may be administered to mammals, including humans, in combination with one or more pharmaceutically acceptable carriers and/or diluents to form a pharmaceutical composition.

The required dosage of the active substance will vary depending on the age, weight and conditions of the patient to be treated as well as on the administration route and on the duration of the desired treatment.

The pharmaceutical compositions, which may be for, e.g., topical, eye, oral, intravenous, subcutaneous or intramuscular administration, can be prepared in a conventional way using the conventional excipients. Compositions for topical application such as, e.g., creams, lotions or pastes, may be, e.g., prepared by admixing the active ingredient with a conventional oleaginous or emulsifying excipient. Lotions for topical administration may contain, e.g., from 10 mg/ml to 100 mg/ml of active substance and be applied up to 7 times a day to the affected area.

Formulations in buffer or physiological saline or other appropriate excipient may be suitable as eyedrop formulation.

Formulations for oral, administration such as, e.g., tablets or capsules, may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinil pyrrolidone; disaggregating agents, e.g. a starch, alginic acid, alginates or sodium starch glycolate; effervescing mixtures; dyestuff; sweeteners; wetting agents, such as lecithin, polysorbates, laurysulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride.

The solutions for intravenous injections or infusione may contain as carrier, for example, sterile water or, preferably, they may be in the form of sterile, aqueous, isotonic saline solutions.

The compounds of the invention may be administered either as such as in the form of pharmaceutically acceptable salts or complexes.

Examples of salts are acid addition salts with both inorganic acids, such as, for instance hydrochloric, hydrobromic, sulphuric and phosphoric acid, and organic acid such as, for instance, maleic, citric, acetic, benzoic, succinic, ascorbic and tartaric acid.

Examples of complexes are, e.g. zinc or iron complexes.

METHODS

1) Construction of Plasmids

Synthetic DNA fragments were obtained by synthesizing oligonucleotides with overlapping sequences on an automatic DNA synthesizer Applied Biosystem 380B model. Nucleotide sequences were determined by the dideoxy method following subcloning of fragments into M13 vectors (Messing J.: Methods Enzymol, 101 p. 20–78, 1983).

Restriction enzymes, ligase and polymerase were used as recommended by manufacturers, E. coli cells were transformed according to standard procedures (Maniatis T., Frisch E. F. and Sambrook J.: Molecular cloning. A laboratory manual. Cold Spring Harbour Laboratory, Cold Spring Harbour, N.Y. 1982).

2) Mutagenesis

The synthetic sequence for wild type bFGF, either the human or the bovine form, was subcloned in an M13 phage vector. Single strand forms of the recombinant phage vectors were grown according to the published methods (Messing J.: Methods Enzymol, 101 p. 20–78, 1983). 20 ng of these M13 single strand DNAs were heated at 95° C. in 10 mM Tris-HCl pH 7.5., 0.1 mM EDTA, 50 mM NaCl for 5 min and annealed to convenient oligonucleotides by stepwise cooling to room temperature. Successively, the following components were added: ATP to a final concentration of 0.4 mM; dCTP, dGTP, dTTP to 0.12 mM; dATP to 0.04 mM; 1 unit of Klenow fragment of the E. coli DNA polymerase I and 0.5 units of T4 DNA ligase (Boehringer Mannheim). Final volume was 50 µl of 35 mM Tris-HCl pH 7.5, 0.1 mM EDTA, 6 mM MgCl2, 0.006 mM DTT. After incubation for 12 hours at 15° C., the DNA was used to transfect E. coli JM 101 cells according to published procedures (Maniatis T., Frisch E. F. and Sambrook J.: Molecular cloning. A laboratory manual. Cold Spring Harbour Laboratory, Cold Spring Harbour, N.Y. 1982).

The oligonucletoides used to cause the desired mutations were radiolabeled using 150 µCi ($\gamma$-32 P) ATP (New England Nuclear, 6000 Ci/mmol), in 70 mM Tris-HCl buffer pH 8. containing 10 mM MgCl2, 5 mM DTT and 10 units of T4 Polynucleotide Kinase (Boehringer Mannheim) in a 50 µl reaction mixture which was incubated for 30 min at 37° C. The labeled oligonucleotides were then used for plaque hybridization to the mutagenized phage DNAs.

Hybridization proceded overnight at 65° C. in 10 mM Tris-HCl pH 8 containing 3x SSC, 0.1% SDS, 10x Denhardt's and 0.2 mg/ml denatured salmon sperm DNA.

Nitrocellulose Filters were washed for 30 min in 0.4x SSC, 0.1% SDS at 65° C. with several changes and exposed overnight to X-ray films. Plaques indicating positive hybridization were selected for Sanger dideoxynucleotide sequencing using the Amersham M13 Sequencing Kit.

3) Induction and Analysis of Gene Expression

Luria broth with tetraciclin (3 µg/ml) was used to grow plasmid bearing cells. M9 medium supplemented with 0.4% glucose, 0.4% casamino acids and 10 mg/ml thiamine was used for induction of gene expression under triptophan promoter.

After 6 hours of growth in M9 medium without triptophan, cells were harvested by centrifugation. Aliquots of bacterial cultures were pelleted, resuspended with sample loading buffer and analyzed by SDS-PAGE according to Laemmli (Laemmli U. K.: Cleavage of structural proteins during the assembly of the head of bacteriophage T4, Nature 227, p. 680–685, 1970).

Alternatively, cells were disrupted with lysozyme or by sonication and the soluble and insoluble fractions, separated by centrifugation, were analyzed separately. After electrophoresis, gels were stained with Coomassie blue for total cell proteins.

Western blottings were probed with polyclonal rabbit antiserum raised against synthetic peptides with bFGF derived sequences. Vectastain ABC kits (Vector Laboratories, California USA) containing biotinylated goat anti-rabbit IgG as secondary antibodies were used as recommended by the manufacturers.

Legends to Figures

FIG. 1. Schematic representation of the different natural forms of basic FGF isolated to date. The 155-amino acid form has been deduced from the cDNA nucleotide sequence.

FIG. 2. The amino acid sequence of human and bovine FGF is illustrated. The two sequences differ in positions 121 and 137. The amino acids corresponding to the bovine form are shown in bold character.

Figure 3B:
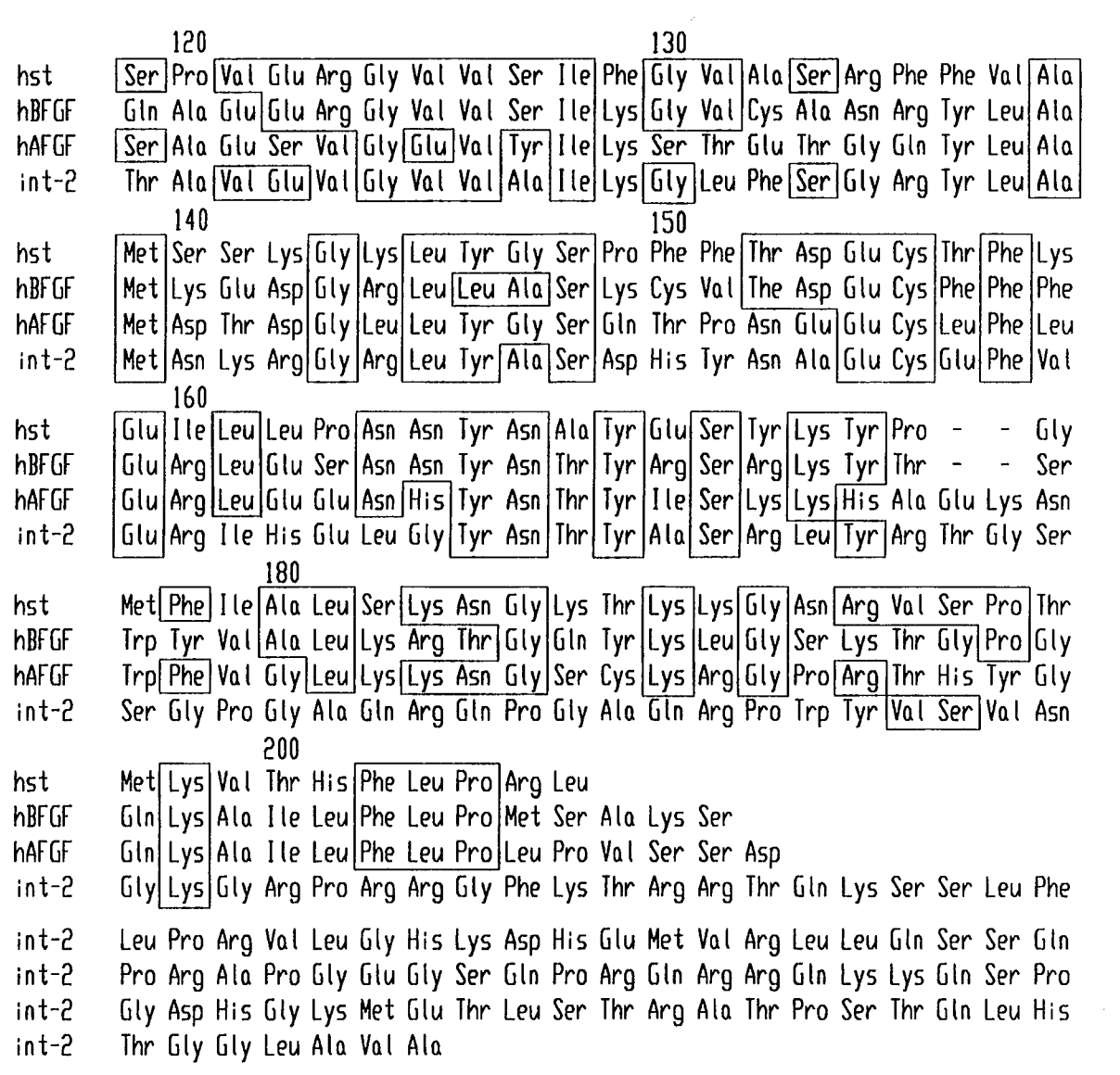

FIGS. 3A-B. This figure has already been published (Yoshida T., Miyagawa K., Odagiri H., Sakamoto H., Little P. F. R., Terada M. and Sugimura T.: Genomic sequence of hst, a transforming gene encoding a protein homologous to fibroblast growth factors and the int-2-encoded protein. Proc. Natl. Acad. Sci. USA 84 p. 7305–7309, 1987).

Entire amino acid sequences of the hst protein, human basic FGF (hbFGF), human acidic FGF (hAFGF) and the mouse int-2 protein are aligned and compared. Dashes indicate gaps inserted for optimal alignment. Residues identical to the hst sequence are boxed. Numbers above the sequence lines refer to the hst residues.

FIGS. 4A-G. Schematic representation of basic FGF derivatives. Numbers refer to the 155-amino acid form. Filled regions represent the deleted amino acid sequences. Black points represent single amino acid substitutions.

Figure 5A:
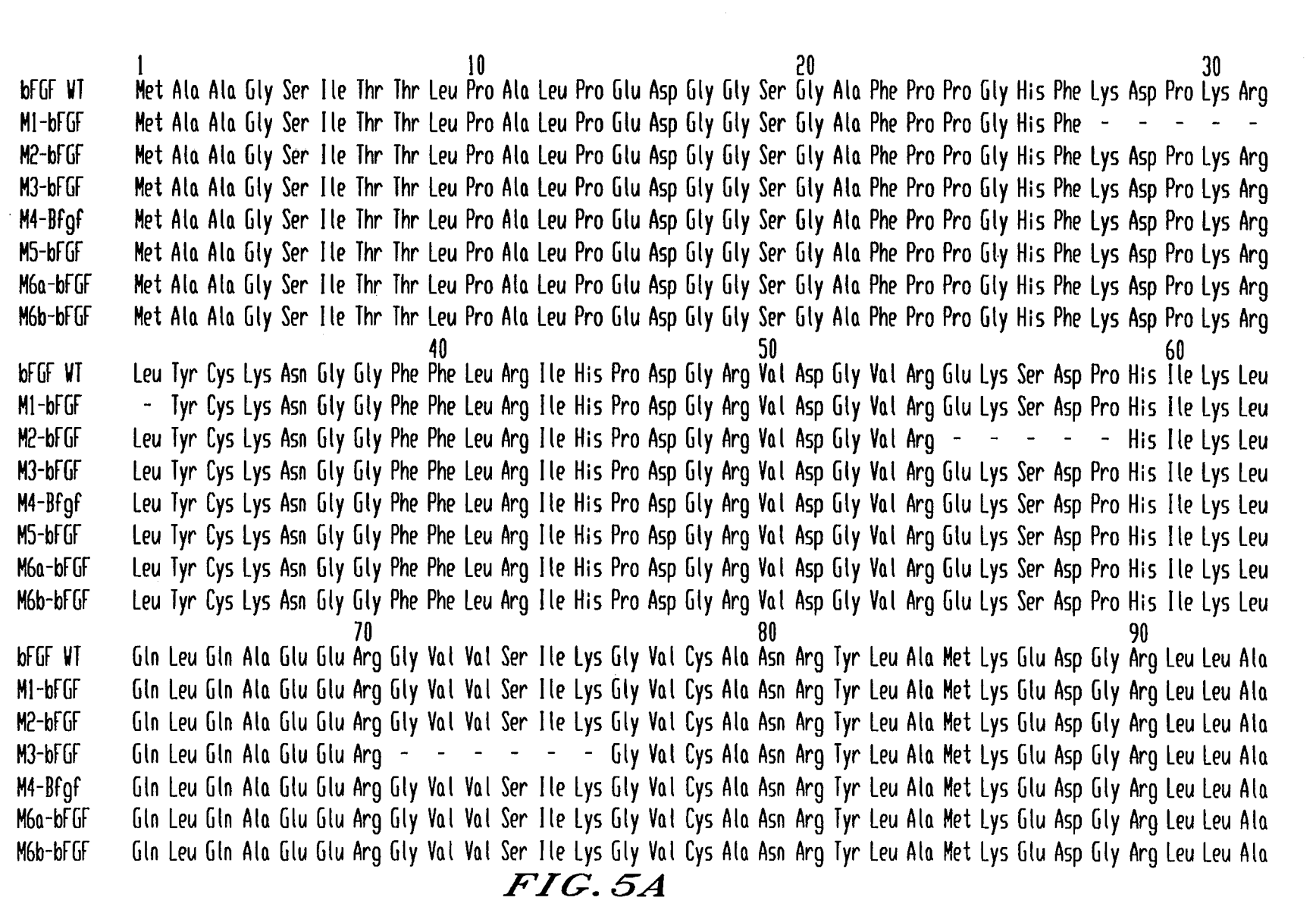

FIGS. 5A-B. The entire amino acid sequences of human bFGF and of its mutants are aligned. Dashes indicate deleted amino acids. Asteriscs represent single amino acid substitutions.

FIG. 6. Nucleotide sequence of human and bovine bFGF. This sequence was synthetically reconstructed and used for the expression of bFGF. The codons for the first 20 amino acids, indicated with an asterisc, have been modified without altering the corresponding amino acid residues. The codons coding for the two amino acids which are different in the bovine sequence are underscript.

FIG. 7. pDS20 represents the general plasmid background which has been utilized for the construction of the bFGF expression plasmids. Replacement of the galK gene with the bFGF gene and insertion of the expression signals Ptrp and the Shine-Dalgarno sequence "cII" from phage lambda bring to the construction of pFC80.

Discussion and Conclusions

The present invention concerns the isolation of new molecular derivatives of basic FGF. The basic FGF molecule of reference can be of either human or bovine origin.

These new derivatives, obtained by recombinant DNA techniques, are deletion or substitution mutants of the 155-amino acid form of bFGF. It is known from the literature that human or bovine basic FGF can be isolated in different forms whose only difference is the length of the $NH_2$-terminal extension. In particular, it seems that bFGFs as short as the 126-amino acid form or as long as the 157-amino acid form are equally active.

The authors of the present invention have carried out mutations in regions of the bFGF molecule, well distinct from this heterogeneous NH2-terminal domain. They have used, as example, the 155-amino acid form. It is obvious, therefore, that the modifications representing the object of the present invention can be carried out also on other forms of the bFGF as, for example, the ones ranging from the 126- to the 157-amino acid form.

As previously stated, the new molecules of the invention can act as antagonists and/or superagonists of the wild-type bFGF molecule. As already mentioned before, antagonists of bFGF could be, in particular, valuable tools for the inhibition of tumoral angiogenesis. Superagonists of bFGF could display improved pharmacological properties compared to the native sequence.

The evaluation of the biological activity of the compounds of the present invention has allowed to individuate some regions of the bFGF molecule which appear to be particularly important for the biological and biochemical properties of bFGF.

The identification of such regions, in particular the regions deleted in the derivatives M1-bFGF, M2-bFGF and M3-bFGF, suggests that further mutations (substitutions, deletions or modifications) in the same regions might lead to therapeutically improved bFGF derivatives.

The present invention includes these further mutations within its scope.

As already said, the present invention also concerns a recombinant DNA procedure for the production of these new molecular entities. Interestingly, this procedure can be successfully applied to the production of the wild-type bFGF, as well. Again, all these considerations are valid for the human and bovine basic FGF sequences.

The recombinant DNA procedure, disclosed within the text of the present invention, is based on strains of the bacterium *E. coli* transformed with plasmid DNA carrying the gene coding for the desired FGF molecule. Of course, the authors of the present invention are aware of the fact that other recombinant DNA procedure have already been disclosed and published (Iwane M., Kurokawa T., Sasada R., Seno M., Nakagawa S., Igarashi K.: Expression of cDNA encoding human basic fibroblast growth factor in *E. coli* Biochem.Biophis. Res.Commun. 146 p. 470–477, 1987).

However, the procedure, described here, presents characteristics of novelty and yields quantities of recombinant bFGF never described before.

One of the major characteristics of this procedure is the type of *E. coli* strain used as host for the production of basic FGF. It is known, in fact, that the type of strain is one of the major parameters influencing the heterologous gene expression in *E. coli* (Harris T.J.R. and Emtage J.S.: Expression of heterologous genes in *E. coli* Microbiological Sciences 3, p. 28–31, 1986).

According to the present invention, it has been found that *E. coli* strains of type B are very efficient hosts for the production of a recombinant bFGF, as well as for bFGF derivatives. Indeed, the same bFGF expression vectors, when inserted in other *E. coli* strain (type K-12, type C, etc) do not yield as much bFGF.

A second characteristic of the present procedure is the introduction of some "optimized codons" within the genes coding for the different bFGF molecules. The authors have, in fact, found that it was necessary to modify a certain number of DNA codons, keeping the same amino acid sequence, in order to increase levels of expression. The preferred DNA coding sequence is disclosed within the text of the present invention (see FIG. 6).

These two characteristics, the type of strain used as host and the optimized codons, constitute the novelty aspects of the present recombinant DNA procedure for the production of bFGF and its mutants. These two aspects, applied to basic FGF, have never been mentioned or published in the scientific literature, to date.

We claim:

1. A human or bovine basic fibroblast growth factor derivative wherein amino acid residues 27 through 32 (Lys-Asp-Pro-Lys-Arg-Leu) have been deleted, the numbering of the above amino acid residues corresponding to the 155-amino acid form of human or bovine basic FGF.

2. A human or bovine basic fibroblast growth factor of claim 1 having an N-terminus selected from the naturally occurring microheterogeneous N-termini of human or bovine basic fibroblast growth factors.

3. A method for the production recombinant derivatives of human or bovine bFGF comprising producing a peptide of claim 1 or 2 an *E. coli* type B strain.

* * * * *